United States Patent [19]

O'Lenick, Jr. et al.

[11] Patent Number: 5,162,472

[45] Date of Patent: Nov. 10, 1992

[54] FREE RADICAL SILICONE POLYMERS

[75] Inventor: Anthony J. O'Lenick, Jr., Lilburn, Ga.

[73] Assignee: Siltech Inc., Norcross, Ga.

[21] Appl. No.: 737,452

[22] Filed: Jul. 29, 1991

Related U.S. Application Data

[63] Continuation-in-part of Ser. No. 597,188, Oct. 9, 1990, Pat. No. 5,120,812.

[51] Int. Cl.$^5$ .................. C08F 30/08; C08F 283/00
[52] U.S. Cl. .................. 526/279; 525/479; 528/32; 528/28; 528/26
[58] Field of Search .................. 526/279; 525/479

[56] References Cited

U.S. PATENT DOCUMENTS 3,782,940  1/1974  Ohto et al. .................. 96/36
4,585,670  4/1986  Liu .................. 427/54.1
4,837,289  6/1989  Mueller et al. .................. 526/279
5,120,812  6/1992  O'Lenick et al. .................. 528/28

*Primary Examiner*—John C. Bleutge
*Assistant Examiner*—Margaret W. Glass

[57] ABSTRACT

The present invention deals with the composition, and application of novel silicone compounds, useful as softening, anti-tangle, and conditioning agents for use in personal care, textile and related applications. The properties of these novel compounds containing silicone which makes them well suited for these applications is the fact that they are substantive to fibers, hair and skin and also very mild to the skin and eyes. The incorporation of a silicone component into the molecule results in several additional desirable properties heretofore unattainable. The polymers are more elastomeric rather than resinous, are more oxygen permeable and can be made more hydrophobic.

10 Claims, No Drawings ized amines.

FREE RADICAL SILICONE POLYMERS

This application is a continuation-in-part of co-pending Ser. No. 07/597,188, filed Oct. 9, 1990, now U.S. Pat. No. 5,120,812.

BACKGROUND OF THE INVENTION

1. Field of the Invention

The present invention deals with the composition, and application of novel silicone compounds, useful as softening, anti-tangle, and conditioning agents for use in personal care, textile and related applications. The properties of these novel compounds containing silicone which makes them well suited for these applications is the fact that they are substantive to fibers, hair and skin and also very mild to the skin and eyes. The incorporation of a silicone component into the molecule results in several additional desirable properties heretofore unattainable. The polymers are more elastomeric rather than resinous, are more oxygen permeable and can be made more hydrophobic.

2. Arts and Practices

The prior practices for providing softening, anti-tangle, and conditioning properties for use in personal care, textile and related applications has been incorporation of quaternary compounds. These materials have been used for many years despite some significant drawbacks including irritation, negative impact on the aquatic environment, build up and yellowing of the substrate upon which they are applied.

Standard quaternary compounds are prepared by quaternization of a tertiary amine with such agents as benzyl chloride or di-methyl sulfate or di-ethyl sulfate or methyl chloride. These materials are relatively inexpensive but offer several key disadvantages. These include yellowing of fabrics, a tendency to build-up upon repeated treatment, and variability in hand (i.e. softness and feel). Standard softeners used are selected from the following classes:

Class #1. Alkyl Imidazoline Quaternary Compounds made from the quaternization of an imidazoline made by reacting diethylenetriamine, and a high molecular weight fatty acid such as stearic acid. The standard quaternizing agents are di-ethyl sulfate, or methyl chloride, or di-methyl sulfate, or methyl chloride or benzyl chloride.

Class #2. Alkyl or dialkyl tertiary amines quaternized with benzyl chloride or di-ethyl sulfate or methyl chloride or di-methyl sulfate Class #3. Quaternary compounds of ethoxylated, propoxylated or nonalkoxylated amido amines derived from the reaction of a high molecular weight fatty acid like stearic acid and a polyamine like diethylene triamine. The standard quaternizing agents are di-ethyl sulfate or di-methyl sulfate or methyl chloride or benzyl chloride.

Class #4. Amido amine salts derived from partially acid neutralized amines.

Phosphobetaines are examples of more recent attempt to attain a substantive low irritation compound. U.S. Pat. No. 4,215,064 to Lindemann et al issued Jul. 29, 1980 teaches that phosphobetaines can be prepared by the reaction of a phosphate or phosphite salt with epichlorohydrin under aqueous conditions. U.S. Pat. No. 4,283,541 to O'Lenick, et al, issued Aug. 11, 1981 teaches the process for the preparation of the phosphobetaines described in Lindemann (U.S. Pat. No. 4,215,064).

U.S. Pat. No. 4,336,385 issued June, 1982 to Mayhew and O'Lenick, teaches that certain phosphated imidazoline derivatives are useful in some cosmetic products.

U.S. Pat. No. 4,800,077 to O'Lenick et al issued January, 1989, teaches that nonirritating quats can be prepared by reacting guerbet alcohols and their alkoxylates with epichlorohydrin and tertiary amines. Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

Many attempts have been made to obtain a cationic polymeric silicone compound suitable for use in cosmetic and personal care products. One approach has been to use hydrosilation technology to make alkoxylated silicone polymers, used as raw materials in this invention. These materials do not have the substantivity desired to make them suitable for use as fiber lubricants or antistats.

A surprising feature of the compounds of the present invention is their liquid nature, mild nature to skin and eye and compatibility in anionic cationic and nonionic systems. This makes the materials of the present invention very useful in personal care products. The references cited herein are incorporated by reference to the extent applicable. Ratios and percentages are by weight and temperatures are Celsius unless otherwise stated.

THE INVENTION

Object of the Invention

It is the object of the current invention to provide a novel series of silicone polymers. The incorporation of the critical silicone group gives increased substantivity to the polymer, lowers irritation and provides excellent antistatic, comb out properties and softening to hair and skin. The incorporation of a silicone component into the molecule results in several additional desirable properties heretofore unattainable. The polymers are more elastomeric rather than resinous, are more oxygen permeable and can be made more hydrophobic.

It is another object of the current invention to provide a novel vinyl silicone monomer used as an intermediate in the preparation of the compounds of the present invention.

It is still another objective of the current invention to provide personal care compositions which contain an effective conditioning amount of the compounds of the current invention. That effective conditioning concentration will vary from 0.1 to 20% of the composition. The compounds of the present invention have outstanding compatibility with anionic, nonionic and cationic surfactant systems.

SUMMARY OF THE INVENTION

The present invention is directed to free radical polymers which contain silicone as one of the functional groups polymerized. The compounds of the invention are prepared by the free radical polymerization of a novel silicone polymer having a reactive vinyl group.

The compounds of the current invention are prepared by the free radical reaction of a silicone monomer and other monomers selected from the following;

$R^1$ is derived from the following silicone monomers

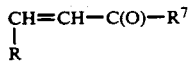

and

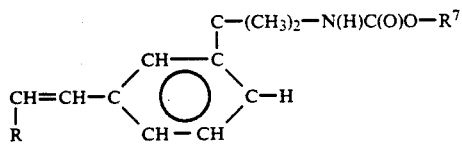

$R^7$ is

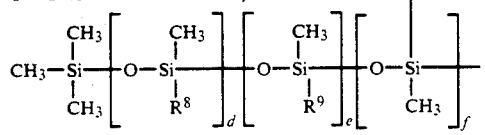

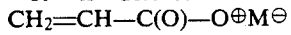

R is selected from $CH_3$ or H;

$R^2$ is derived from the following monomer $CH_2=CH-C(O)-O^\ominus M^\oplus$

Acrylic acid and methacrylic acid is available from Dow.

$R^3$ is derived from the following monomer;

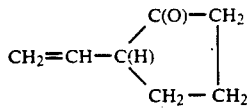

Vinyl pyrrolidone is available commercially from BASF.

$R^4$ is derived from the following monomer;

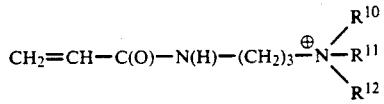

$R^{10}$, $R^{11}$ and $R^{12}$ are selected from H, methyl and ethyl;

These monomers are available from CPS Corporation.

$R^5$ is derived from the following monomer $CH_2=CH-C(O)-NH_2$

Acrylamide is available from Dow Chemical.

$R^6$ is derived from the following monomer;

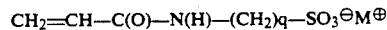

These materials are available from Lubrizol Inc.

These materials are reacted in a solvent, typically water under the influence of a free radical catalyst. Free radical polymerization is well known to those skilled in the art.

An additional aspect of the invention is the vinyl silicone compound used as a reactive intermediate. One of the compounds conforms to the following structure;

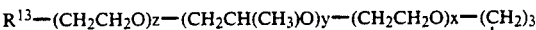

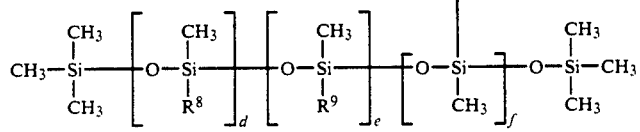

d is an integer from 0 to 200;
e is an integer from 0 to 200;
f is an integer from 1 to 200;
$R^8$ is selected from $-(CH_2)_nCH_3$ and phenyl;
n is an integer from 0 to 10;
$R^9$ is $-(CH_2)_3-(OCH_2CH_2)x-(OCH_2CH(CH_3))y-(OCH_2CH_2)z-OH$;
x, y and z are integers and are independently selected from 0 to 20;

$R^{13}$ is

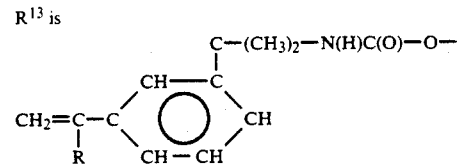

An additional silicone intermediate compound useful in the preparation of the compounds of the present invention conform to the following structure;

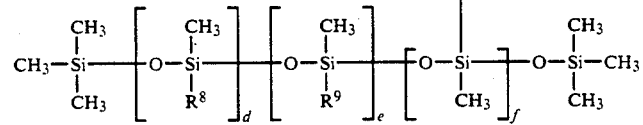

d is an integer from 0 to 200;
e is an integer form 0 to 200;
f is an integer from 1 to 200;
$R^8$ is selected from $-(CH_2)_nCH_3$ and phenyl;

n is an integer from 0 to 10;
$R^9$ is $-(CH_2)_3-(OCH_2CH_2)x-(OCH_2CH(CH_3))y-(OCH_2CH_2)z-OH$;

x, y and z are integers and are independently selected from 0 to 20;

$R^{13}$ is $CH=CH-C(O)-$
         |
         R

PREFERRED EMBODIMENT

In one preferred embodiment the polymer has in addition to the silicone portion, at least one amine component present (i.e. d is at least 1). These molecules have enhanced antistatic properties.

EXAMPLES

Raw Materials

Preparation of Silicone Intermediates

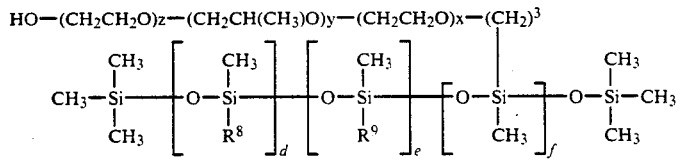

The silicone intermediates are available from Siltech Inc. Norcross Ga.

| | Example 1 | Example 2 | Example 3 | Example 4 |
|---|---|---|---|---|
| x | 0 | 1 | 2 | 5 |
| y | 0 | 0 | 5 | 5 |
| z | 0 | 0 | 2 | 5 |
| d | 50 | 50 | 100 | 15 |
| e | 2 | 0 | 0 | 1 |
| f | 1 | 1 | 1 | 1 |
| $R^8$ | Methyl | Methyl | Phenyl | Phenyl |

| | Example 5 | Example 6 | Example 7 | Example 8 |
|---|---|---|---|---|
| x | 10 | 5 | 5 | 20 |
| y | 10 | 1 | 10 | 20 |
| z | 10 | 5 | 0 | 20 |
| d | 20 | 200 | 50 | 10 |
| e | 2 | 0 | 1 | 1 |
| f | 1 | 1 | 1 | 1 |
| $R^8$ | Methyl | Methyl | Ethyl | Ethyl |

CLASS 1: Acrylic Esters of Examples 9-16

General Procedure

Acrylic esters are prepared by the reaction of the silicone intermediates 1-8 with one mole of acrylic acid. The reaction mass is heated to 140 to 180 C. and the theoretical amount of water is stripped off.

72.0 grams of acrylic acid is added to a clean glass vessel equipped with agitation and a thermometer. Next, the specified amount of the specified silicone intermediate Examples 1-8 is added. The reaction mass is heated to 140 to 180 C. and the theoretical amount of water distills off. The vinyl containing silicone ester is used without additional purification.

EXAMPLES 9-16

| | Grams of Acrylic Acid | Example Number Grams |
|---|---|---|
| Example 9 | 72.0 | 4,220.0 Gm. of Example 1 |
| Example 10 | 72.0 | 3,860.0 Gm. of Example 2 |
| Example 11 | 72.0 | 12,747.0 Gm. of Example 3 |
| Example 12 | 72.0 | 1,714.0 Gm. of Example 4 |
| Example 13 | 72.0 | 1,355.0 Gm. of Example 5 |
| Example 14 | 72.0 | 15,415.0 Gm. of Example 6 |
| Example 15 | 72.0 | 6,789.0 Gm. of Example 7 |

The products of examples 9-16 conform to the following structure;

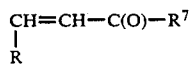

PREPARATION OF VINYL POLYURETHANE SILICONE POLYMERS

General Procedure

The vinyl reactive silicone urethanes are prepared by the reaction of the silicone intermediates 1-8 with the specified amount of Benzene-1-(1-isocyanoato-1-methylethyl)-3-(1-methylethenyl) (an unsaturated aliphatic isocynate).

The material is a bifunctional monomer marketed by Cynamide under the name TMI. It conforms to the following structure;

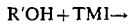

The reaction of TMI with a hydroxyl group is as follows;

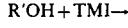

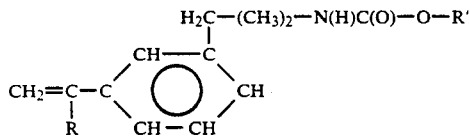

Procedure 202.0 grams of TMI is added to a clean glass vessel equipped with agitation and a thermometer. Next, the specified amount of the specified silicone intermediate Examples 1-8 is added. The reaction mass is heated to 140 to 180 C. and the urethane is formed over a 3 to 5 hour period. The vinyl containing silicone urethane is used without additional purification in the preparation of the polymers of the present invention.

EXAMPLES 17-24

| Example | Grams of TMI | Example Number Grams |
| --- | --- | --- |
| Example 17 | 202 | 4,220.0 Gm. of Example 1 |
| Example 18 | 202 | 3,860.0 Gm. of Example 2 |
| Example 19 | 202 | 12,747.0 Gm. of Example 3 |
| Example 20 | 202 | 1,714.0 Gm. of Example 4 |
| Example 21 | 202 | 1,355.0 Gm. of Example 5 |
| Example 22 | 202 | 15,415.0 Gm. of Example 6 |
| Example 23 | 202 | 6,789.0 Gm. of Example 7 |
| Example 24 | 202 | 5,043.0 Gm. of Example 8 |

CLASS 2: VINYL AMINO COMPOUNDS

Examples 25-28

$$CH_2=CH-C(O)-N(H)-(CH_2)_3-\overset{\oplus}{N}\overset{R^{10}}{\underset{R^{12}}{-R^{11}}}$$

| Example | $R^{10}$ | $R^{11}$ | $R^{12}$ |
| --- | --- | --- | --- |
| 25 | Methyl | Methyl | Hydrogen |
| 26 | Methyl | Methyl | Methyl |
| 27 | Ethyl | Methyl | Hydrogen |
| 26 | Ethyl | Methyl | Methyl |
| 28 | Ethyl | Ethyl | Methyl |

CLASS 3: VINYL ANIONIC MATERIALS

Examples 29-32

| $CH_2=CH-C(O)-N(H)-(CH_2)_q-SO_3^{\ominus}M^{\oplus}$ | | |
| --- | --- | --- |
| Example | q | M |
| 29 | 3 | H |
| 30 | 4 | H |
| 31 | 3 | Na |
| 32 | 3 | K |

CLASS 4: VINYL CARBOXYLIC COMPOUNDS

Example 33

Acrylic Acid    $CH_2=CH-C(O)-OH$

CLASS 5: VINYL LACTOONES

Examples 34

Vinyl pyrrolidone

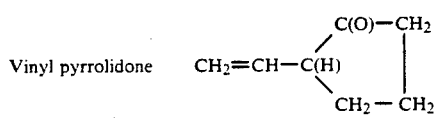

CLASS 6: VINYL AMIDES

Example 35

Acrylamide    $CH_2=CH-C(O)-NH_2$

PREPARATION OF SILICONE POLYMERS

Examples 36-63

General Polymerization Procedure

The polymerization of the vinyl containing compounds is achieved by utilizing free radical catalyst in a low oxygen containing solvent, most commonly water. The water is deionized and sparged with nitrogen to remove dissolved oxygen contained therein immediately prior to use. Then, the specified amount of the treated dionized water is added to a suitable glass vessel. Most commonly, 50 to 80% of the total weight of the batch is water. The specified amount of the specified monomers are then added under agitation. Nitrogen is continuously sparged and the temperature is raised to about 50 C. Once the temperature has reached 50 and the nitrogen has been bubbled through the reaction mass for thirty minutes, a free radical initiator is added. Many peracids, like t-butyl-perbenzoate, t-butyl-hydroperoxide and inorganic free radical initators like stannic chloride can be used. The preferred initator is azobisisobutylnitrile. The reaction is exothermic and cooling is used to keep the temperature below 90 C.

The molecular weight is monitored by viscosity and both increase as the reaction continues.

EXAMPLE 36

To the specified number of grams (5,000 Gm.) of deionized water, which has just been spargred with nitrogen for 30 minutes, is added the specified amount (4,200 grams) of Class 1 monomer (Ex #17). Next add the specified amount (0 grams) of Class 2 monomer (Ex #25) followed by the specified amount (0 grams) of Class 3 monomer (Ex #29) followed by the specified amount (0 grams) of Class 4 monomer (Ex #33) followed by the specified amount (0 grams) of Class 5 monomer (Ex #34) followed by the specified amount (0 grams) of Class 6 monomer (Ex #35), under good agitation and nitrogen sparge. The temperature is raised to about 50 C. Once the temperature has reached 50 and the nitrogen has been bubbled through the reaction mass for thirty minutes, the specified amount of the specified catalyst (azobisisobutylnitrile) is added. The catalyst may be optimally added in smaller increments of one quarter of the total needed waiting 30 minutes between additions. The viscosity will raise as the polymerization occurs. The temperature raises to about 90 C. and is cooled with cooling water as needed to prevent the temperature from reaching 90 C. The desired polymer is used as prepared.

EXAMPLES 37-63

The above procedure is repeated only substituting the specified amount and type of monomer, catalyst and water specified.

| | Example 36 | Example 37 | Example 38 | Example 39 |
| --- | --- | --- | --- | --- |
| Class 1 | Ex #17 | Ex #18 | Ex #19 | Ex #20 |
| | 4,200 Gm. | 3,860 Gm. | 12,747 Gm. | 1,714 Gm. |
| Class 2 | Ex #25 | Ex #26 | Ex #27 | Ex #28 |
| | 157.0 Gm. | 171.0 Gm. | 185.0 Gm. | 216.0 Gm. |
| Class 3 | Ex #29 | Ex #30 | Ex #31 | Ex #32 |
| | 193.0 Gm. | 207.0 Gm. | 215.0 Gm. | 231.0 Gm. |
| Class 4 | Ex #33 | Ex #33 | Ex #33 | Ex #33 |
| | 72.0 Gm. | 0 Gm. | 0 Gm. | 0 Gm. |
| Class 5 | Ex #34 | Ex #34 | Ex #34 | Ex #35 |
| | 110.0 Gm. | 1,100 Gm. | 110.0 Gm. | 0 Gm. |
| Class 6 | Ex #35 | Ex #35 | Ex #35 | Ex #35 |

-continued

|  | | | | |
|---|---|---|---|---|
|  | 158.0 Gm. | 1,580 Gm. | 0 Gm. | 0 Gm. |
| Water | 5,000 Gm. | 10,000 Gm. | 20,000 Gm. | 5,000 Gms |
| Catalyst | | These examples used 0.05% by weight of batch of azobisisobutylnitrile | | |

|  | Example 40 | Example 41 | Example 42 | Example 43 |
|---|---|---|---|---|
| Class 1 | Ex #21 | Ex #22 | Ex #23 | Ex #24 |
|  | 13.5 Gm. | 15.4 Gm. | 67.8 Gm. | 50.4 Gm. |
| Class 2 | Ex #25 | Ex #26 | Ex #27 | Ex #28 |
|  | 157.0 Gm. | 171.0 Gm. | 185.0 Gm. | 216.0 Gm. |
| Class 3 | Ex #30 | Ex #30 | Ex #30 | Ex #30 |
|  | 0 Gm. | 0 Gm. | 0 Gm. | 0 Gm. |
| Class 4 | Ex #33 | Ex #33 | Ex #33 | Ex #33 |
|  | 0 Gm. | 0 Gm. | 0 Gm. | 0 Gm. |
| Class 5 | Ex #34 | Ex #34 | Ex #34 | Ex #34 |
|  | 0 Gm. | 110.0 Gm. | 1,100 Gm. | 11.0 Gm. |
| Class 6 | Ex #35 | Ex #35 | Ex #35 | Ex #35 |
|  | 0 Gm. | 0 Gm. | 0 Gm. | 0 Gm. |
| Water | 250 Gm. | 600 Gm. | 3,000 Gm. | 150 Gm. |
| Catalyst | | These examples used 0.05% by weight of batch of azobisisobutylnitrile | | |

|  | Example 44 | Example 45 | Example 46 | Example 47 |
|---|---|---|---|---|
| Class 1 | Ex #9 | Ex #10 | Ex #11 | Ex #12 |
|  | 4,200 Gm. | 3,860 Gm. | 12,747 Gm. | 1,714 Gm. |
| Class 2 | Ex #25 | Ex #25 | Ex #26 | Ex #27 |
|  | 0 Gm. | 157.0 Gm. | 171.0 Gm. | 185.0 Gm. |
| Class 3 | Ex #30 | Ex #30 | Ex #29 | Ex #30 |
|  | 0 Gm. | 0 Gm. | 193.0 Gm. | 207.0 Gm. |
| Class 4 | Ex #33 | Ex #33 | Ex #33 | Ex #33 |
|  | 0 Gm. | 0 Gm. | 0 Gm. | 72.0 Gm. |
| Class 5 | Ex #34 | Ex #34 | Ex #34 | Ex #34 |
|  | 0 Gm. | 0 Gm. | 0 Gm. | 0 Gm. |
| Class 6 | Ex #35 | Ex #35 | Ex #35 | Ex #35 |
|  | 0 Gm. | 0 Gm. | 0 Gm. | 0 Gm. |
| Water | 4,200 Gm. | 5,000 Gm. | 15,000 Gm. | 2,500 Gm. |
| Catalyst | | These examples used 0.05% by weight of batch of azobisisobutylnitrile | | |

|  | Example 48 | Example 49 | Example 50 | Example 51 |
|---|---|---|---|---|
| Class 1 | Ex #13 | Ex #14 | Ex #15 | Ex #16 |
|  | 1,355 Gm. | 15,415 Gm. | 6,789 Gm. | 5,043 Gm. |
| Class 2 | Ex #28 | Ex #25 | Ex #26 | Ex #27 |
|  | 216.0 Gm. | 1,570 Gm. | 1,710 Gm. | 1,850 Gm. |
| Class 3 | Ex #31 | Ex #32 | Ex #29 | Ex #30 |
|  | 215.0 Gm. | 231.0 Gm. | 193.0 Gm. | 207.0 Gm. |
| Class 4 | Ex #33 | Ex #33 | Ex #33 | Ex #33 |
|  | 0 Gm. | 0 Gm. | 0 Gm. | 0 Gm. |
| Class 5 | Ex #34 | Ex #34 | Ex #34 | Ex #34 |
|  | 110.0 Gm. | 110.0 Gm. | 110.0 Gm. | 1,100 Gm. |
| Class 6 | Ex #35 | Ex #35 | Ex #35 | Ex #35 |
|  | 0 Gm. | 0 Gm. | 0 Gm. | 158.0 Gm. |
| Water | 2,000 Gm. | 22,000 Gm. | 10,000 Gm. | 10,000 Gm. |
| Catalyst | | These examples used 0.05% by weight of batch of t-butyl-hydroperoxide (Lucidol TBHP-70-X) | | |

|  | Example 52 | Example 53 | Example 54 | Example 55 |
|---|---|---|---|---|
| Class 1 | Ex #17 | Ex #18 | Ex #19 | Ex #20 |
|  | 4,200 Gm. | 3,860 Gm. | 12,747 Gm. | 1,714 Gm. |
| Class 2 | Ex #25 | Ex #25 | Ex #25 | Ex #25 |
|  | 0 Gm. | 0 Gm. | 0 Gm. | 0 Gm. |
| Class 3 | Ex #30 | Ex #30 | Ex #30 | Ex #30 |
|  | 0 Gm. | 0 Gm. | 0 Gm. | 0 Gm. |
| Class 4 | Ex #33 | Ex #33 | Ex #33 | Ex #33 |
|  | 0 Gm. | 0 Gm. | 0 Gm. | 0 Gm. |
| Class 5 | Ex #34 | Ex #34 | Ex #34 | Ex #34 |
|  | 4,200 Gm. | 110.0 Gm. | 30,000 Gm. | 100.0 Gm. |
| Class 6 | Ex #35 | Ex #35 | Ex #35 | Ex #35 |
|  | 0 Gm. | 0 Gm. | 0 Gm. | 0 Gm. |
| Water | 10,000 Gm. | 5,000 Gm. | 55,000 Gm. | 1,000 Gm. |
| Catalyst | | These examples used 0.07% by weight of batch of t-butyl-hydroperoxide (Lucidol TBHP-70-X) | | |

|  | Example 56 | Example 57 | Example 58 | Example 59 |
|---|---|---|---|---|
| Class 1 | Ex #21 | Ex #22 | Ex #23 | Ex #24 |
|  | 135.5 Gm. | 154.1 Gm. | 67.9 Gm. | 50.4 Gm. |
| Class 2 | Ex #25 | Ex #25 | Ex #25 | Ex #25 |
|  | 1,570 Gm. | 0 Gm. | 0 Gm. | 0 Gm. |
| Class 3 | Ex #29 | Ex #29 | Ex #29 | Ex #29 |
|  | 0 Gm. | 1,930 Gm. | 0 Gm. | 0 Gm. |
| Class 4 | Ex #33 | Ex #33 | Ex #33 | Ex #33 |
|  | 0 Gm. | 0 Gm. | 720 Gm. | 0 Gm. |
| Class 5 | Ex #34 | Ex #34 | Ex #34 | Ex #34 |
|  | 0 Gm. | 0 Gm. | 0 Gm. | 1,100 Gm. |
| Class 6 | Ex #35 | Ex #35 | Ex #35 | Ex #35 |
|  | 0 Gm. | 0 Gm. | 0 Gm. | 0 Gm. |
| Water | 1,000 Gm. | 1,000 Gm. | 1,000 Gm. | 2,000 Gm. |
| Catalyst | | These examples used 0.07% by weight of batch of t-butyl perbenzoate | | |

|  | Example 60 | Example 61 | Example 62 | Example 63 |
|---|---|---|---|---|
| Class 1 | Ex #10 | Ex #11 | Ex #12 | Ex #13 |
|  | 420.0 Gm. | 386.0 Gm. | 1,274 Gm. | 171.4 Gm. |
| Class 2 | Ex #26 | Ex #26 | Ex #26 | Ex #26 |
|  | 216.0 Gm. | 2,160 Gm. | 2.16 Gm. | 2,160 Gm. |
| Class 3 | Ex #30 | Ex #30 | Ex #30 | Ex #30 |
|  | 0 Gm. | 0 Gm. | 0 Gm. | 0 Gm. |
| Class 4 | Ex #33 | Ex #33 | Ex #33 | Ex #33 |
|  | 0 Gm. | 0 Gm. | 0 Gm. | 0 Gm. |
| Class 5 | Ex #34 | Ex #34 | Ex #34 | Ex #34 |
|  | 110.0 Gm. | 1,100 Gm. | 11.0 Gm. | 0 Gm. |
| Class 6 | Ex #35 | Ex #35 | Ex #35 | Ex #35 |
|  | 0 Gm. | 0 Gm. | 0 Gm. | 0 Gm. |
| Water | 500 Gm. | 1,000 Gm. | 5,000 Gm. | 10,000 Gm. |
| Catalyst | | These examples used 0.05% by weight of batch of t-butyl perbenzoate | | |

APPLICATION DATA

Applications of the Compounds of The Invention

Compounds of this invention were compared to standard compounds commercially available using AATCC Test Method 117-1979. The color fastness heat test uses a 400 F. (205 F.) hot iron which is applied for 60 and 180 seconds. The color is rated on a 1-5 basis for yellowness, (5 being the most yellow).

| Compound | CAS Number | Yellowness |
|---|---|---|
| Class #1 Compound | 68122-86-1 | 4 |
| Class #2 Compound | 61789-81-9 | 4 |
| Class #3 Compound | 65098-88-6 | 5 |
| Class #4 Compound | 68308-45-2 | 4 |
| Example #53 | | 1 |
| Example #45 | | 2 |
| Example #62 | | 2 |

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. THe swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Product Example #53 | 11 |

| Rinse Conditioner (Wet Comb Out Test) | |
|---|---|
| Product | Time in Seconds |
| Product Example #42 | 13 |
| Stearyldimethylbenzyl ammonium chloride | 12 |

The compounds of the present invention are useful as softening, anti-tangle, and conditioning agents. They are nonirritating, substantive materials which are oxygen permable. Their use is therefore recommended for use in personal care, textile and related applications.

The properties of these novel compounds containing silicone which makes them well suited for these applications is the fact that they are substantive to fibers, hair and skin and also very mild to the skin and eyes.

The compounds of the present invention are useful as softening, anti-tangle, and conditioning agents. They are nonirritating, substantive materials which are oxygen permable. Their use is therefore recommended for use in personal care, textile and related applications.

The properties of these novel compounds containing silicone which makes them well suited for these applications is the fact that they are substantive to fibers, hair and skin and also very mild to the skin and eyes.

What is claimed:

1. A silicone containing polymer prepared by the free radical polymerization reaction of a vinyl silicone containing monomer selected from the group consisting of;

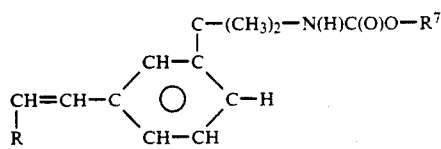

and

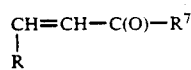

wherein:
R is selected from $CH_3$ or H;
$R^7$ is

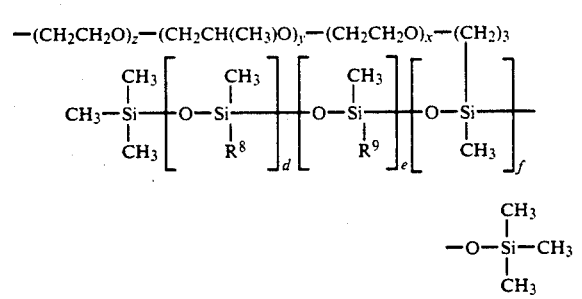

d is an integer from 0 to 200;
e is an integer from 0 to 200;
f is an integer from 1 to 200;
$R^8$ is selected from the group consisting of $-(CH_2)_nCH_3$ and phenyl;
n is an integer from 0 to 10;

$R^9$ is $-(CH_2)_3-(OCH_2CH_2)_x-(OCH_2CH(CH_3))_y-(OCH_2CH_2)_z-OH$;

x, y and z are integers independently selected from 0 to 20;

with one or more additional compounds conforming to the following structure;

wherein;
M is selected from the group consisting of H, Na, K, Li, and $NH_4$;

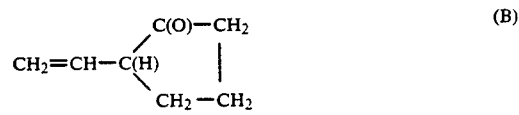

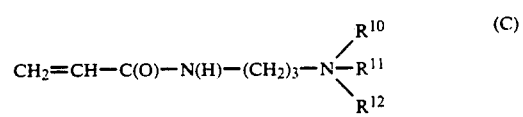

wherein;
$R^{10}$, $R^{11}$ and $R^{12}$ are selected from the group consisting of H, methyl and ethyl;

and

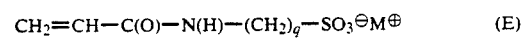

wherein;
q is an integer ranging from 1 to 5.

2. A silicone containing polymer of claim 1 wherein the vinyl silicone containing monomer conforms to the following structure;

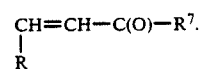

3. A silicone containing polymer of claim 1 wherein the vinyl silicone containing monomer conforms to the following structure;

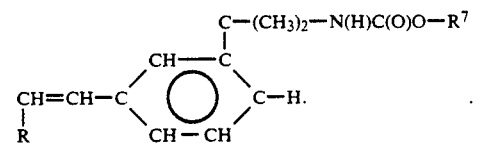

4. A silicone containing polymer of claim 1 wherein said vinyl containing silicone monomer is reacted with compounds from each group conforming to the following structure;

M is selected from the group consisting of H, Na, K, Li, and $NH_4$;

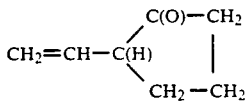 (B)

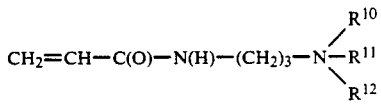 (C)

$R^{10}$, $R^{11}$ and $R^{12}$ are selected from the group consisting of H, methyl and ethyl;

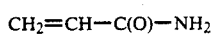 (D)

and

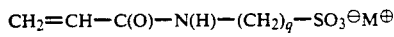 (E)

q is an integer ranging from 1 to 5.

5. A silicone containing polymer of claim 1 wherein said vinyl reactive silicone is reacted with a compound conforming to the following structure;

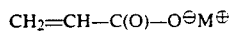

wherein;
M is selected from the group consisting of H, Na, K, Li, and $NH_4$.

6. A silicone containing polymer of claim 1 wherein said vinyl reactive silicone is reacted with a compound conforming to the following structure;

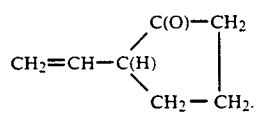

7. A silicone containing polymer of claim 1 wherein said vinyl reactive silicone is reacted with a compound conforming to the following structure;

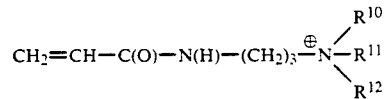

wherein;
$R^{10}$, $R^{11}$ and $R^{12}$ are selected from the group consisting of H, methyl and ethyl.

8. A silicone containing polymer of claim 1 wherein said vinyl reactive silicone is reacted with a compound conforming to the following structure;

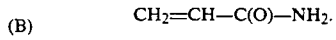

9. A silicone containing polymer of claim 1 wherein said vinyl reactive silicone is reacted with a compound conforming to the following structure;

wherein;
q is an integer ranging from 1 to 5.

10. A silicone containing polymer prepared by the free radical polymerization reaction of a vinyl silicone containing monomer selected from the group consisting of;

and

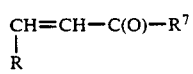

wherein;
R is selected from $CH_3$ or H;
$R^7$ is

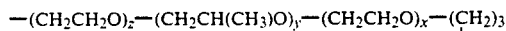

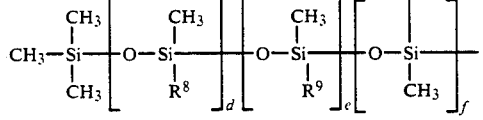

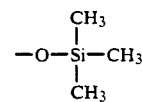

d is an integer from 0 to 200;
e is an integer from 0 to 200;
f is an integer from 1 to 200;
$R^8$ is selected from the group consisting of —$(CH_2)_nCH_3$ and phenyl;
n is an integer from 0 to 10;
$R^9$ is —$(CH_2)_3$—$(OCH_2CH_2)x$—$(OCH_2CH(CH_3))y$—$(OCH_2CH_2)z$—OH;
x, y and z are integers independently selected from 0 to 20.

* * * * *